United States Patent
Ooyauchi et al.

(10) Patent No.: US 6,748,786 B2
(45) Date of Patent: Jun. 15, 2004

(54) METAL TUBULAR BODY AND MANUFACTURING METHOD THEREOF

(75) Inventors: Tetsuya Ooyauchi, Kanagawa (JP); Masayuki Okano, Tokyo (JP)

(73) Assignees: Terumo Kabushiki Kaisha, Tokyo (JP); Okano Kogyo Co., Ltd., Hyogo (JP)

(*) Notice: Subject to any disclaimer, the term of this patent is extended or adjusted under 35 U.S.C. 154(b) by 0 days.

(21) Appl. No.: 10/375,085

(22) Filed: Feb. 28, 2003

(65) Prior Publication Data
US 2003/0211352 A1 Nov. 13, 2003

(30) Foreign Application Priority Data
May 7, 2002 (JP) .......................... 2002-131195

(51) Int. Cl.[7] .............. B21D 51/10; B21C 1/00
(52) U.S. Cl. ............. 72/370.14; 428/577; 428/586; 428/600; 72/370.15
(58) Field of Search ............... 428/600, 586, 428/577; 138/170, 156, 171; 72/370.14, 370.15

(56) References Cited

U.S. PATENT DOCUMENTS

| | | | | |
|---|---|---|---|---|
| 922,990 A | * | 5/1909 | White | 428/579 |
| 2,058,556 A | * | 10/1936 | Blair | 72/76 |
| 2,187,259 A | * | 1/1940 | Barnhart | 604/117 |
| 2,286,971 A | * | 6/1942 | Murray | 86/53 |
| 2,855,929 A | | 10/1958 | Hein, Jr. | |
| 3,173,200 A | | 3/1965 | Dunmire et al. | |
| 3,289,675 A | * | 12/1966 | Dunmire | 604/272 |
| 4,603,806 A | * | 8/1986 | Watanabe et al. | 228/152 |
| 4,672,734 A | | 6/1987 | Kawada et al. | |
| 4,785,868 A | | 11/1988 | Koenig, Jr. | |
| 5,074,555 A | * | 12/1991 | Meredith | 473/323 |
| 5,951,528 A | * | 9/1999 | Parkin | 604/239 |
| 2003/0089414 A1 | * | 5/2003 | Ooyauchi et al. | 138/171 |
| 2003/0127149 A1 | * | 7/2003 | Ooyauchi et al. | 138/177 |

FOREIGN PATENT DOCUMENTS

| | | | |
|---|---|---|---|
| DE | 3802445 A1 | * | 8/1989 |
| JP | 48-41968 | * | 6/1973 |
| JP | 6-225940 A | | 8/1994 |
| JP | 2001-259028 | | 9/2001 |
| JP | 2002-058747 | | 2/2002 |

* cited by examiner

Primary Examiner—John J. Zimmerman
(74) Attorney, Agent, or Firm—Burns, Doane, Swecker & Mathis, L.L.P.

(57) ABSTRACT

A metal tubular body of small diameter having a varying wall thickness is provided. The tubular body has a minimum inner diameter of up to 2 mm and a maximum wall thickness of up to 0.5 mm, and the wall thickness varies along its longitudinal axis.

12 Claims, 5 Drawing Sheets

METAL TUBULAR BODY AND MANUFACTURING METHOD THEREOF

BACKGROUND OF THE INVENTION

1. Field of the Invention

This invention relates to a metal tubular body and its manufacturing method. More specifically, this invention relates to a metal tubular body having a wall thickness varying along its longitudinal axis which can be used in such applications as a pin, an injection needle, a connector, and a liquid crystal electron gun for TV, as well as its manufacturing method.

2. Prior Art

Metal tubular bodies of small diameter, for example, those having an inner diameter of up to 2 mm used as a pin, an injection needle, or a connector for medical applications, or an electron gun for TV is often required to have a wall thickness that varies from part to part. Such tubular body with varying wall thickness has been produced by using a tubular body having a constant thickness and grinding its outer or inner surface.

The tubular body manufactured by such method, however, suffered from the marks left on the surface that had been made in the grinding, and the resulting tubular body was defective. In addition, surface grinding was difficult to perform when the tubular body had a small diameter. Surface grinding also required an additional step, and resulted in a complicated manufacturing process that was unfeasible for mass production.

In spite of such situation, there is a practical need for a tubular body of smaller diameter. For example, patients requiring routine injection using an injection needle as in the case of diabetes patients conducing regular insulin injection are waiting for a needle wherein pain upon needle insertion has been reduced to its minimum.

An injection needle having an excessively reduced diameter, however, suffer from insufficient flow of the drug solution therethrough making the injection of the drug solution difficult. Accordingly, the diameter of the injection needle can be reduced only to a limited degree.

Tubular bodies having a varying diameter such as those having a tapered lateral shape or a stepped lateral shape have been manufactured by rolling a metal sheet, and repeatedly drawing the rolled metal sheet. The tubular body manufactured by such method, however, has a constant wall thickness along its full length despite the difference in the diameter. The wall thickness of such tubular body is, therefore, determined by the section of smallest diameter, and the tubular body manufactured inevitably suffers from insufficient strength since the section with a larger diameter has an excessively reduced wall thickness.

SUMMARY OF THE INVENTION

It is therefore an object of the present invention to obviate the prior art problems as described above and provide a metal tubular body having a varying wall thickness. Another object of the invention is to provide a method for manufacturing such metal tubular body.

In order to attain the object as described above, this invention provides a metal tubular body wherein at least a part of a wall thickness of the tubular body varies along its longitudinal axis, and wherein the tubular body has a minimum inner diameter of up to 2 mm and a maximum wall thickness of up to 0.5 mm.

The present invention also provides a method for manufacturing a metal tubular body wherein at least a part of a wall thickness of the tubular body varies along its longitudinal axis, comprising the steps of: punching a sheet blank in the developed shape of the tubular body from a metal sheet such that the metal sheet and the sheet blank remain partly joined, said metal sheet having at least a part of a thickness which varies in the direction of the longitudinal axis of the finished tubular body; pressing the sheet blank into a tubular shape; and cutting the pressed sheet blank from the metal sheet to thereby produce the tubular body.

The present invention also provides a method for manufacturing a metal tubular body wherein wall thickness of the tubular body varies along its longitudinal axis, comprising the steps of: punching a sheet blank in the developed shape of the tubular body from a metal sheet such that the metal sheet and the sheet blank remain partly joined; pressing the sheet blank into a tubular shape such that the pressed sheet blank in tubular shape has a thickness which varies along the longitudinal axis; and cutting apart the metal sheet and the sheet blank at the part where they remain joined to thereby produce the tubular body.

In the method for manufacturing a metal tubular body according to the present invention, the sheet blank that has been pressed in tubular shape may be welded along its seam.

This invention also provides a metal tubular body manufactured by the method of the present invention.

BRIEF DESCRIPTION OF THE DRAWINGS

FIGS. 3A and 3B are schematic views showing the manufacturing process of the tubular body by the present method. FIG. 3A shows the metal sheet before the punching, and FIG. 3B shows the sheet blank punched out of the metal sheet. The sheet blank is in the developed shape of the tubular body to be manufactured.

FIGS. 4A and 4B are also schematic views showing the manufacturing process of the tubular body by the present method. FIG. 4A shows the sheet blank that has been curved by pressing, and FIG. 4B shows the sheet blank that has been pressed in U-shape.

FIG. 5 is also a schematic view showing the manufacturing process of the tubular body by the present method. FIG. 5 shows the sheet blank that has been pressed in tubular shape.

DETAILED DESCRIPTION OF THE INVENTION

Next, the method for manufacturing the metal tubular body and the metal tubular body produced by such method of the present invention are described by referring to the drawings.

The metal tubular body of the present invention has a characteristic feature that its wall thickness varies along its longitudinal axis. The "varying wall thickness" includes both the case wherein the distal and proximal ends of the tubular body have different wall thickness with the wall thickness of the tubular body continuously varying, namely, gradually increasing or reducing along its longitudinal axis, and the case wherein the tubular body includes a section whose wall thickness is different from other parts of the tubular body.

When the wall thickness of the tubular body continuously varies along its length, the variation of the wall thickness along the longitudinal axis of the tubular body may be either consistent along the full length so that the tubular body has a tapered side shape, or inconsistent so that the tubular body has a side shape curved in the form of an exponential of logarithmic curve.

Typical tubular bodies including a section whose wall thickness is different from other parts of the tubular body are tubular bodies comprising two or more sections each having different wall thickness wherein the wall thickness varies discontinuously at the boundary between the two adjacent sections, for example, a tubular body including only one section whose wall thickness is different from, namely, thicker or thinner than other parts of the tubular body, and a tubular body with a stepped shape comprising two or more sections of different diameters, each section having different wall thickness.

Figure 1A:
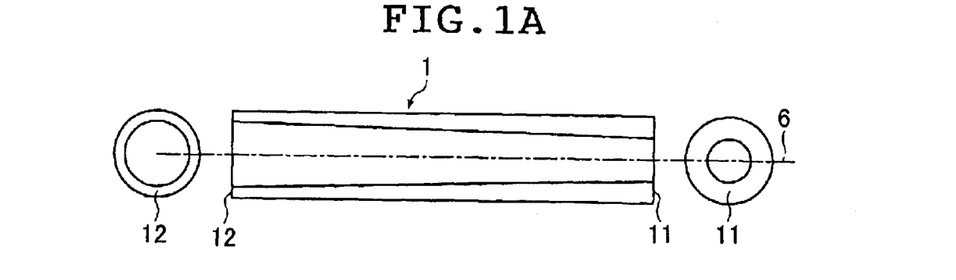
FIGS. 1A, 1B, and 1C are front, side and back views of the tubular bodies according to some embodiments of the present invention.
Figure 1B:
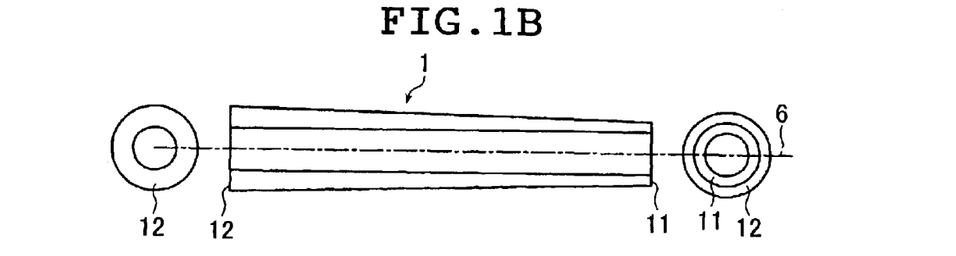
Figure 1C:
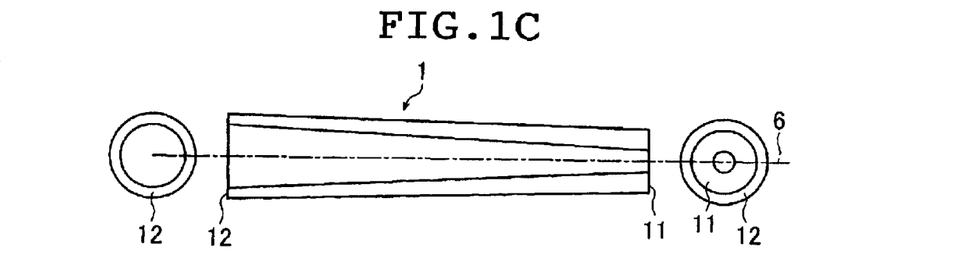

FIGS. 1A, 1B, and 1C are front, side and back views of typical embodiments of the metal tubular body wherein the wall thickness continuously varies along its longitudinal axis. In FIGS. 1A, 1B, and 1C, tubular body 1 has a distal end 11 and a proximal end 12, and the tubular body 1 extends along axis 6. The tubular body 1 of FIG. 1A is a straight hollow tube of circular cross section having an equal outer diameter at the distal end 11 and proximal end 12. The inner diameter of the distal end 11, however, is smaller than that of the inner diameter of the proximal end 12 with the wall thickness gradually reducing from the distal end 11 to the proximal end 12 along the axis 6. The tubular body 1 of FIG. 1B is a tapered hollow tube of circular cross section having an outer diameter of the distal end 11 which is smaller than the outer diameter of the proximal end 12. The inner diameters of the distal end 11 and the proximal end 12, however, are equal with the wall thickness gradually increasing from the distal end 11 to the proximal end 12 along the axis 6. The tubular body 1 of FIG. 1C is a tapered hollow tube of circular cross section having an outer diameter and an inner diameter of the distal end 11 which are respectively smaller than the outer diameter and the inner diameter of the proximal end 12, and the wall thickness gradually reducing from the distal end 11 to the proximal end 12 along the axis 6.

Figure 2A:
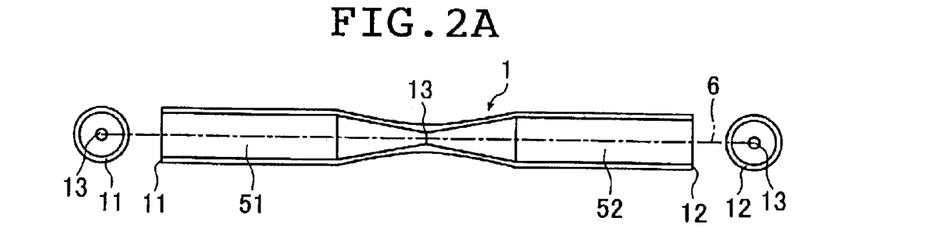
FIGS. 2A, 2B, and 2C are front, side and back views of the tubular bodies according to other embodiments of the present invention.
Figure 2B:
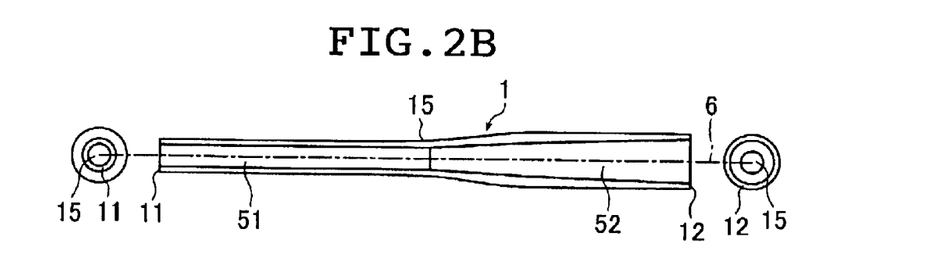
Figure 2C:
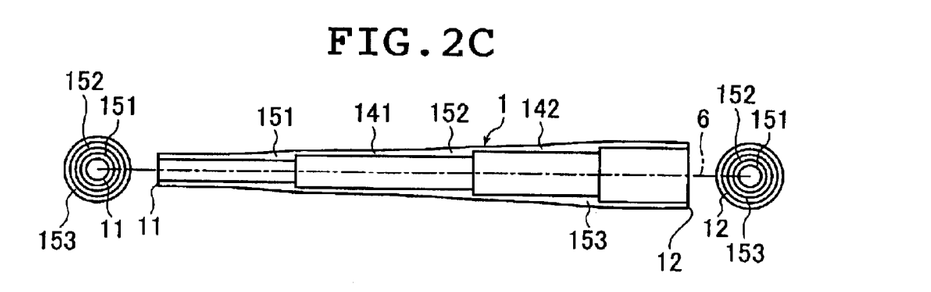

FIGS. 2A, 2B, and 2C are front, side and back views of typical embodiments of the metal tubular body having a section whose wall thickness is different from other parts of the tubular body. In FIGS. 2A, 2B, and 2C, tubular body 1 has a distal end 11 and a proximal end 12, and the tubular body 1 extends along axis 6. The tubular body 1 of FIG. 2A is a hollow tube wherein an orifice section 13 of smaller inner diameter is provided at the central portion of the straight tube of circular cross section, and the orifice section 13 has a wall which is thicker than other parts of the tubular body. The tubular body 1 of FIG. 2B is a hollow tube of circular cross section having a stepped lateral shape comprising a distal end section 51 of smaller inner and outer diameters, a proximal end section 52 of larger inner and outer diameters, and a transient section 15 between the distal end section 51 and the proximal end section 52. The wall thickness increases along the axis 6 to the midpoint of the tubular body, namely, from the proximal end 12 toward the transient section 15, and then reduces toward the proximal end 12. The tubular body 1 of FIG. 2C is a hollow tube of circular cross section comprising a distal end section 51 of smaller inner and outer diameters, a proximal end section 52 of larger inner and outer diameters, and intermediate sections 141 and 142 therebetween. The inner diameters of the intermediate sections 141 and 142 are different from one another, and different from the inner diameters of the distal end section 51 and the proximal end section 52. The inner diameter changes in a discontinuous manner between the sections of different inner diameters (between the distal end section 51 and the intermediate section 141, between the intermediate section 141 and the intermediate section 142, and between the intermediate section 142 and the proximal end section 52) while the inner diameters are constant in each section (in the distal end section 51, the intermediate section 141, the intermediate section 142, and the proximal end section 52). On the other hand, the outer diameter gradually increases from the distal end 11 to the proximal end 12, and transient sections 151, 152, and 153 are provided between the distal end section 51 and the intermediate section 141, between the intermediate section 141 and the intermediate section 142, and between the intermediate section 142 and the proximal end section 52, respectively. The wall thickness of the distal end section 51, the proximal end section 52, and the intermediate sections 141 and 142 are different from each other, and the wall thickness increases toward the proximal end 52 in the transient sections 151, 152, and 153.

Next, application of such metal tubular body having a wall thickness that varies along its longitudinal axis is described. The tubular body shown in FIG. 1A having a wall whose thickness increases toward the distal end is adapted for use as an injection needle having an edge of special shape at its distal end since the tubular body of this type has a larger grinding and polishing margin and therefore enjoys an increased design freedom for the shape of the edge formed. In addition, when the tubular body 1 as shown in FIG. 1A which is formed with a groove extending along the outer surface of the distal portion 11 of the needle in the direction of the axis 6 is used for the needle of a double-structure indwelling needle comprising a metal inner needle and a plastic outer needle as disclosed in JP 2002-58747 A and JP 2001-259028 A, access of the needle to the vein can be visually confirmed since the blood will ascend through the groove upon insertion of the needle into the vein. The tubular body 1 shown in FIGS. 1B and 1C has a distal end 11 with a smaller outer diameter, and pain in the injection is alleviated due to the reduced resistance upon puncture of the needle. The wall thickness of the tubular body 1 of FIG. 1C increases toward the distal end 11 with the inner diameter of the tubular body 1 gradually reducing toward the distal end 11 forming a tapered inner surface. As a consequence, when the tubular body 1 is used as an injection needle, the drug solution flowing through the tubular body 1 is limited and the drug solution can be gradually administered at a slow rate without administering a large dose at once. The tubular body 1 of FIG. 2A can be used as an orifice for controlling the flow rate. The tubular bodies 1 of stepped shape shown in FIGS. 2B and 2C are free from the problem of insufficient strength since, despite inclusion of the two or more sections having different diameters, each section has different wall thickness in contrast to the conventional tubular bodies having consistent wall thickness along its full length.

It is to be noted that FIGS. 1 and 2 show typical embodiments of the metal tubular bodies of the present invention, and the shape of the metal tubular bodies of the present invention is not limited to those shown in the drawings. For example, the tubular body may also have a cross section such as quadrilateral, hexagon, or other polygon as well as ellipsoid other than circle shown in FIGS. 1 and 2. With regard to the lateral shape, the tubular body may be a straight tube, or a tapered, stepped, or other non-straight tube as shown in FIGS. 1 and 2. The relation between the lateral shape of the tubular body and the thickness variation in the axial direction is also not particularly limited. To be more specific, the wall thickness may gradually increase or decrease in the direction of the axis 6 while the tubular body has a lateral shape of a straight tube as in the case of the tubular body shown in FIG. 1A. The wall thickness may also gradually increase or decrease in correspondence with the gradual increase or decrease of the outer diameter in the direction of the axis 6 as in the case of the tubular body shown in FIG. 1B. The wall thickness may also gradually increase or decrease in the direction of the axis 6 in reverse correspondence with the gradual increase or decrease of the outer diameter in the direction of the axis 6 as in the case of the tubular body shown in FIG. 1C.

In the present invention, the tubular body typically has an outer diameter of up to 8 mm, and preferably up to 5 mm. When the tubular body is used as an injection needle, it may have an outer diameter of up to 2 mm, preferably up to 1 mm, and more preferably up to 0.4 mm. When the outer diameter is within such range, the tubular body used as an injection needle will experience reduced resistance in its insertion into the skin, and pain associated with the injection will be reduced.

In the present invention, the tubular body typically has the minimum inner diameter of up to 2 mm, preferably up to 1 mm, and more preferably up to 0.5 mm. The term "minimum inner diameter" used herein designates the inner diameter in the case when the tubular body has a consistent inner diameter throughout its length as in the case of the tubular body shown in FIG. 1B, and the smallest inner diameter when the tubular body has two or more inner diameters as in the case of the tubular bodies shown in FIGS. 1A, 1C, and 2A to 2C.

It should be noted that, when the tubular body has two or more inner diameters, the maximum inner diameter of the two or more inner diameters should be up to 5 mm, preferably up to 1.5 mm, and more preferably up to 0.8 mm.

When the tubular body has an inner diameter within such range, the tubular body will enjoy sufficient strength required for a tubular body when the tubular body has an outer diameter within the above-specified range.

Of the two or more different wall thickness of the tubular body of the present invention, the maximum wall thickness is up to 0.5 mm, preferably up to 0.4 mm, more preferably up to 0.3 mm, and most preferably up to 0.2 mm.

Of the two or more different wall thickness of the tubular body of the present invention, the minimum wall thickness is up to 0.4 mm, preferably up to 0.3 mm, more preferably up to 0.2 mm, and most preferably in the range of 0.02 to 0.1 mm.

When the tubular body has the wall thickness as described above the wall thickness is in good balance with the inner and outer diameters as described above and the drug or other liquid can smoothly flow though the lumen without being hindered while the tubular body may retain sufficient strength.

The ratio of the minimum wall thickness to the maximum wall thickness is preferably in the range of 1:10 to 9:10, preferably 1:4 to 9:10, and more preferably 1:2 to 9:10.

When the ratio of the minimum wall thickness to the maximum wall thickness is within such range, the drug or other liquid flowing through the tubular body will not receive excessive resistance when the tubular body is used in the application where a liquid passes through its lumen as in the case of an injection needle, and such situation is quite suitable in view of the function of the tubular body.

In the present invention, the inner surface of the tubular body may preferably have a maximum height difference (Rf) of the surface roughness as defined by JISB-0601-1994 of up to 3 $\mu$m, preferably up to 2 $\mu$m, and more preferably up to 1 $\mu$m. When the tube inner surface has an Rf within the above-specified range, the entire inner surface of the tube will be smooth with no major scratch, and the tubular body will be quite suitable for use as a medical device. When the tubular body is produced by the method of the present invention as will be described below by press machining, the maximum height difference Rf of the inner surface of the tubular body will be within the above-specified range since there is no need to grind the inner surface of the tubular body in order to produce the tubular body with a varying wall thickness.

The tubular body may be made of any suitable metal. For example, it may be made of a steel material such as stainless steel, a nonferrous metal structural material such as aluminum, copper, or titanium, a heat-resistant material such as nickel, cobalt, or molybdenum, a low melting point metal material such as lead or tin, a noble metal material such as gold, silver or platinum, and an alloy thereof.

The tubular body is not limited for its length. When the tubular body is used for an injection needle, however, the length of the tubular body which is inevitably thin walled should be selected to comply with the strength required for the tubular body. For example, the tubular body having a diameter corresponding to the injection needle gage of 25 to 35 which is used for an injection needle should have a hardness of at least 200 Vickers hardness.

Figure 3A:
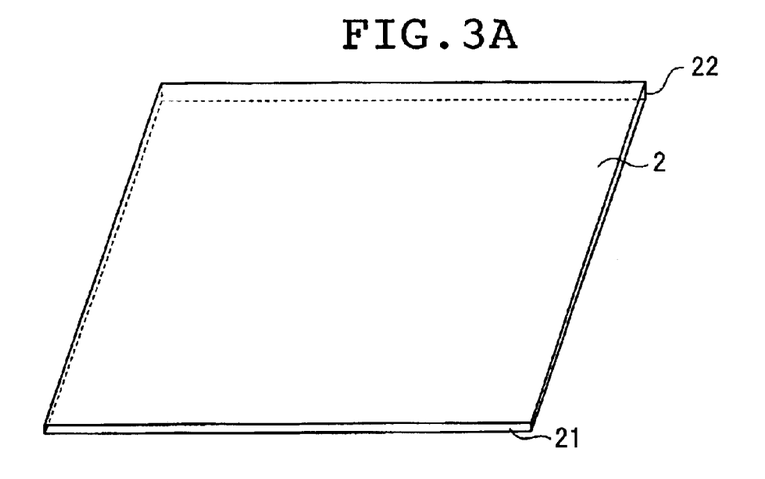
Figure 3B:
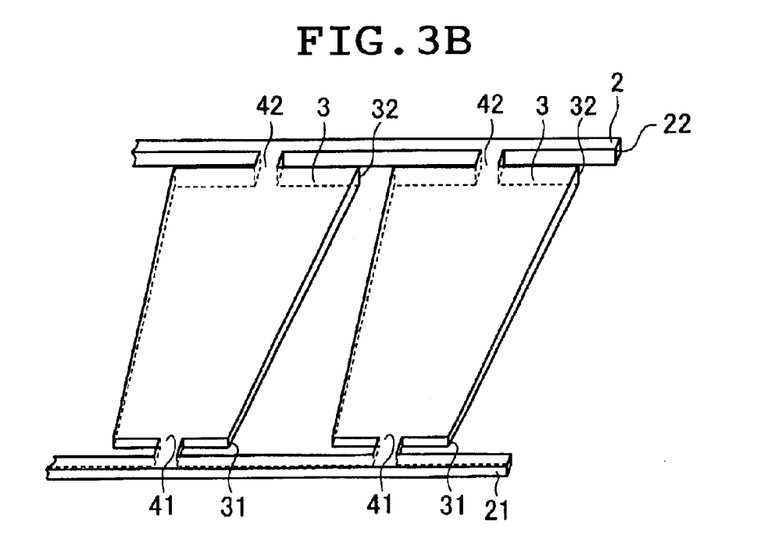
Figure 4A:
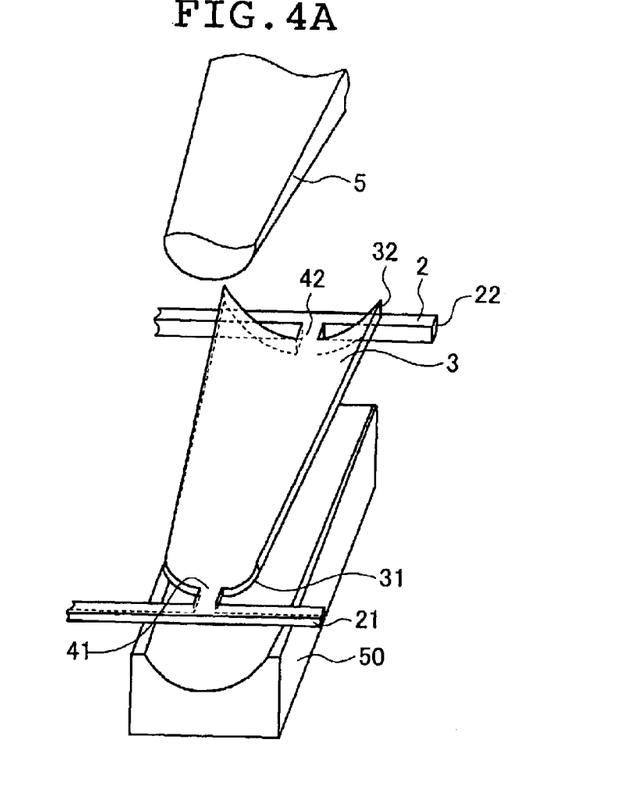
Figure 4B:
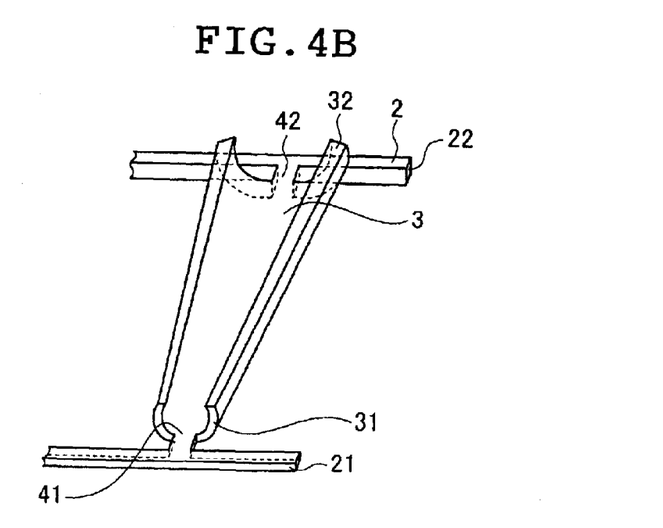
Figure 5:
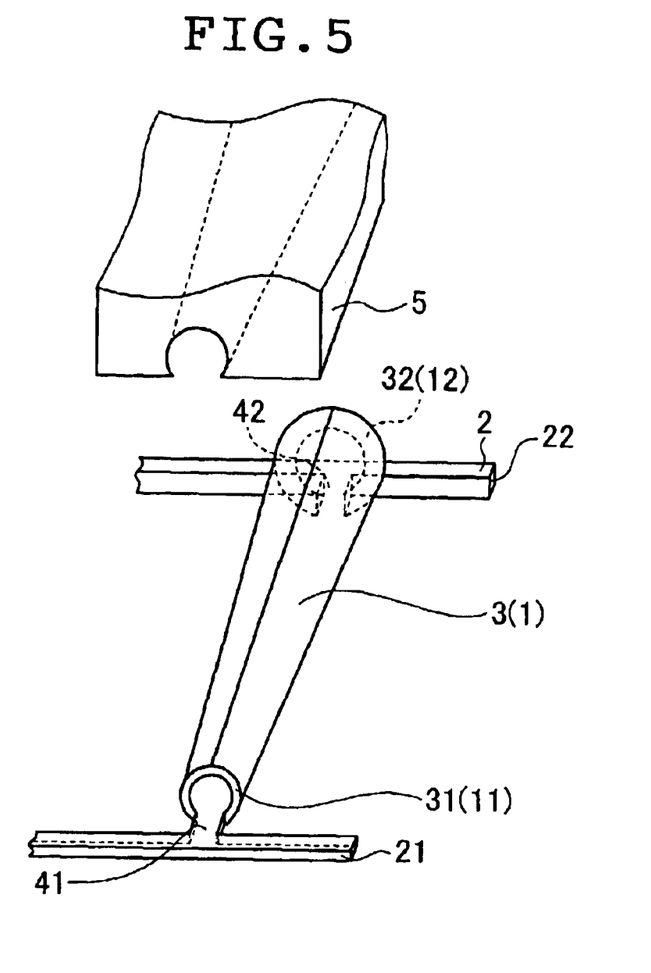

Next, the method for manufacturing the metal tubular body of the present invention is described. FIGS. 3 to 5 schematically illustrate a typical process of manufacturing the metal tubular body according to the method of the present invention. The tubular body produced in FIGS. 3 to 5 is a tapered tube having a circular cross section as shown in FIG. 1B. This tube has an outer diameter of the distal end 11 which is smaller than the outer diameter of the proximal end 12, and the inner diameters of the distal end 11 and the proximal end 12 are equal with the wall thickness gradually increasing from the distal end 11 to the proximal end 12 along the axis 6. It is to be noted that FIGS. 3 to 5 together illustrate the pressing step of the method of the invention.

Since the sheet blank used for manufacturing the tubular body has a shape substantially corresponding to the finished tubular body except for the parts tying the sheet blank to the metal sheet 2, various parts are indicated in the following description by using the term used for the pressed tubular shaped body indicated by numeral 1 in FIG. 5, and the side corresponding to the distal end 11 of the tubular shaped body 1 is referred as the distal side, and the side corresponding to the proximal end 12 is referred to as the proximal side. It is to be noted, however, that the procedure shown by the drawings are presented to facilitate the understanding the method of the present invention, and the present invention is by no means limited by such illustration.

In the method of the present invention, a sheet blank having the developed shape of the finished tubular body is first punched out of a metal sheet having a thickness of up to 0.5 mm which varies in the direction of the longitudinal axis of the finished tubular body. FIG. 3A shows the metal sheet at the start of the present method. As shown in FIG. 3A, the thickness of the metal sheet 2 increases from the distal side 21 corresponding to the distal end of the finished tubular body (the distal end of the tubular shaped body after pressing) to the proximal side 22 corresponding to the proximal end of the finished tubular body (the proximal end of the tubular shaped body after pressing), namely, along the shorter side of the metal sheet 2. Such metal sheet having a thickness varying along the longitudinal axis of the finished tubular body may be a metal sheet that has been preliminarily produced to have the thickness corresponding to the wall thickness desired for the finished tubular body. However, the metal sheet having a thickness varying along the longitudinal axis of the finished tubular body may be the one obtained by pressing a metal sheet having a constant thickness. For example, in the case of the metal sheet shown in FIG. 3A, a metal sheet of constant thickness may be pressed such that the side of the metal sheet corresponding to the distal end of the finished tubular body is pressed to a larger extent than the side of the metal sheet corresponding to the proximal end of the finished tubular body by continuously varying the extent of the pressing along the longitudinal axis of the finished tubular body, namely, in the direction of the shorter side of the metal sheet, to thereby obtain a metal sheet having a thickness varying along the longitudinal axis of the tubular shape finished tubular body as shown in FIG. 3A.

FIG. 3B shows a sheet blank 3 in the developed shape of the tubular body that has been punched out of the metal sheet 2. As shown in FIG. 3B, when the sheet blank 3 in the developed shape of the tubular body is punched out of the metal sheet 2, the sheet blank 3 is not completely punched out of the metal sheet 2, and the sheet blank 3 is left partly tied to the metal sheet 2. The shape of the sheet blank 3 punched out may be selected depending on the final shape of the tubular body having at least two inner diameters. In FIG. 3B, the sheet blank 3 remains partly tied to the metal sheet 2 by ties 41 and 42 respectively located at the center of the cutout lines at the distal and proximal ends 31 and 32 of the sheet blank 3, and the sheet blank 3 that has been punched out has a trapezoidal shape with a side at the distal end 31 which is shorter than the side at the proximal end 32. Since the sheet blank 3 is punched out of the metal sheet 2 shown in FIG. 3A, the thickness of the sheet blank 3 increases along the longitudinal axis of the finished tubular body from the distal side 31 corresponding to the distal end of the finished tubular body to the proximal side 32 corresponding to the proximal end of the finished tubular body, namely, along the longitudinal axis of sheet blank 3.

It is to be noted that the method used in the punching the sheet blank 3 out of the metal sheet 2 is not limited to mechanical punching, and the sheet blank 3 may be thermally punched from the metal sheet 2 by using laser or the like.

Next, the sheet blank 3 is pressed from both above and below as shown in FIG. 4B by using a pair of dies 5. In FIG. 4A, by using an upper die 5 which is convex in combination with a lower die 50 which is concave, the sheet blank 3 is pressed into a curved shape about an axis extending between the ties 41 and 42 connecting the sheet blank 3 and the metal sheet.

In the embodiment shown in FIG. 4A, the sheet blank 3 in trapezoidal shape is pressed into a tapered tube, and therefore, the distal end 31 of the sheet blank 3 is preferably moved upward in relation to the plane of the metal thin plate 4 so that the central axis of the tube 8 will extend parallel to the plane of the metal sheet 2 in the course of the pressing.

FIG. 4B shows the sheet blank 3 after further pressing. In FIG. 4B, the sheet blank 3 is curved even further into U-shape. Pressing of the sheet blank 3 into this latter shape may be achieved by continued pressing with the dies 5 shown in FIG. 4B, or by pressing with dies of other shapes. The sheet blank 3 that has been pressed in U-shape is then pressed in tubular shape using a concave upper die 5 in the manner shown in FIG. 5. As will be readily apparent to one skilled in the art, pressing may be carried out in a number of additional stages using differently shaped dies until the sheet blank has been pressed in tubular shape like that shown in FIG. 5. Furthermore, upper ends of the sheet blank 3 that had been pressed in U-shape shown in FIG. 4B may be further curved into a tubular shape by using a core in addition to the die 5.

As described above, the tubular shaped body 1 having a wall thickness varying along its longitudinal axis is pressed from the metal sheet 2. In FIG. 5, the tubular shaped body 1 is in the shape corresponding to the tubular body of 1B, that is, in the shape of a tapered tube of circular cross section having a thickness gradually increasing from the distal end 11 to the proximal end 12 in the direction of the longitudinal axis of the tube wherein the distal end 11 and the proximal end 12 have the same inner diameter and the distal end 11 has an outer diameter smaller that of the proximal end 12.

It should be noted that, however, it is only required in the present method that the sheet blank that has been pressed into the tubular shape has a wall thickness varying along the longitudinal axis at the time when the pressing has been completed.

Therefore, the method of the present invention is not limited to the use of a metal sheet that has been preliminarily produced to have the thickness of the finished tubular body varying along the longitudinal axis, and it is also allowable that the sheet blank in the developed shape of the finished tubular body that has been punched out of the metal sheet of consistent thickness is pressed so that the sheet blank has the thickness of the finished tubular body varying along the longitudinal axis. Such pressing of the sheet blank for thickness variation may be carried out either simultaneously with or independent from the step of pressing the sheet blank into the tubular shape. To be more specific, the sheet blank of consistent thickness may be pressed into a sheet blank of varying thickness by a procedure similar to the above-described procedure wherein the metal sheet of consistent thickness is pressed into the metal sheet of varying thickness, and then, the thus produced sheet blank with the varying thickness may be pressed into the tubular shape. Alternatively, the step of pressing the sheet blank having a consistent thickness into the sheet blank having the thickness varying along the longitudinal axis of the finished tubular body may be carried out simultaneously with the step of pressing the sheet blank into the tubular shape in one integrated step.

In cases where a fluid will be passed through the lumen of the tubular body manufactured by pressing, for example, when the tubular body is used as an injection needle, the seam of the tubular body must be joined in a liquid-tight manner. Such liquid-tight joining can be accomplished solely by the step of pressing as described above when this step is carried out at a sufficiently high precision. However, other means may be employed to accomplish the liquid-tight joining of the seam of the pressed tubular shaped body. For example, the seam may be joined by using an adhesive. It is, however, preferable to weld the a tubular body along its seam since the tubular body is made of a metal, and in view of its size as thin as 1 mm or less in its outer diameter. The welding process is preferably one which involves the melting of the joint including the base. Preferred examples include laser welding techniques such as carbon dioxide laser welding, YAG laser welding and excimer laser welding. Of these, carbon dioxide laser welding and YAG laser welding are especially preferred because they are widely used, inexpensive and suitable for micromachining.

The pressed sheet blank in the tubular shape can be cut apart from the metal sheet to thereby obtain the tubular body of the present invention. When the tube is welded along its seam for liquid-tight sealing, the tubular body may be obtained by cutting the tubular sheet blank from the metal sheet after the welding.

The tubular body manufactured in this way may be subjected to further processing according to the intended use of the tubular body. For example, if the tubular body is to be used as an injection needle, the distal end of the tubular body is cut at a predetermined angle to the longitudinal axis of the tubular body and the resulting beveled surface is polished to form the needle edge.

EXAMPLES

Next, the present invention is described in further detail by referring to the following Examples which by no means limit the scope of the invention.

Example 1

A hollow tube with a circular cross section as shown in FIG. 1A was produced by a procedure similar to that shown in FIGS. 3 to 5 from a stainless steel (SUS304) sheet. The stainless steel sheet used had a thickness on the side corresponding to the distal end of the finished tubular body of 0.1 mm and a thickness on the side corresponding to the proximal end of the finished tubular body of 0.05 mm, with the thickness gradually reducing from the side corresponding to the distal end to the side corresponding to the proximal end of the finished tubular body in the direction corresponding to the longitudinal axis of the finished tubular body. The tubular body produced was a straight tube having an equal outer diameter at the distal end 11 and proximal end 12. The inner diameter of the distal end 11, however, was smaller than that of the inner diameter of the proximal end 12 with the wall thickness gradually reducing from the distal end 11 to the proximal end 12 along the axis 6. The resulting hollow tube had the size as summarized below:

Distal section
outer diameter: 1 mm, inner diameter: 0.8 mm, wall thickness: 0.1 mm.
Proximal section
outer diameter: 1 mm, inner diameter: 0.9 mm, wall thickness: 0.05 mm
Length: 20 mm
Rf: 0.8 $\mu$m

Example 2

A hollow tube with a circular cross section as shown in FIG. 1B was produced by a procedure similar to that shown in FIGS. 3 to 5 from a stainless steel (SUS304) sheet. The stainless steel sheet used had a thickness on the side corresponding to the distal end of the finished tubular body of 0.05 mm and a thickness on the side corresponding to the proximal end of the finished tubular body of 0.1 mm, with the thickness gradually increasing from the side corresponding to the distal end to the side corresponding to the proximal end of the finished tubular body in the direction corresponding to the longitudinal axis of the finished tubular body. The tubular body produced was a tapered tube having an outer diameter of the distal end 11 which is smaller than the outer diameter of the proximal end 12. The inner diameters of the distal end 11 and the proximal end 12, however, were equal with the wall thickness gradually increasing from the distal end 11 to the proximal end 12 along the axis 6. The resulting hollow tube had the size as summarized below:

Distal section
outer diameter: 0.7 mm, inner diameter: 0.6 mm, wall thickness: 0.05 mm.
Proximal section
outer diameter: 0.8 mm, inner diameter: 0.6 mm, wall thickness: 0.1 mm
Length: 20 mm
Rf: 1.1 $\mu$m

Example 3

A hollow tube with a circular cross section as shown in FIG. 1C was produced by a procedure similar to that shown in FIGS. 3 to 5 from a stainless steel (SUS304) sheet. The stainless steel sheet used had a thickness on the side corresponding to the distal end of the finished tubular body of 0.07 mm and a thickness on the side corresponding to the proximal end of the finished tubular body of 0.05 mm, with the thickness gradually reducing from the side corresponding to the distal end to the side corresponding to the proximal end of the finished tubular body in the direction corresponding to the longitudinal axis of the finished tubular body. The tubular body produced was a tapered tube having an outer diameter and an inner diameter of the distal end 11 which are respectively smaller than the outer diameter and the inner diameter of the proximal end 12, and the wall thickness gradually reducing from the distal end 11 to the proximal end 12 along the axis 6. The resulting hollow tube had the size as summarized below:

Distal section
outer diameter: 0.3 mm, inner diameter: 0.16 mm, wall thickness: 0.07 mm.
Proximal section
outer diameter: 0.7 mm, inner diameter: 0.6 mm, wall thickness: 0.05 mm
Length: 20 mm
Rf: 1.7 $\mu$m

MERITS OF THE INVENTION

The tubular body of the present invention has a wall thickness which varies along its longitudinal axis, and when it is used as an injection needle by forming the distal end to have an outer diameter and a wall thickness smaller the proximal end, pain associated with the insertion of the needle can be reduced without hindering the flow of the drug solution through the tubular body in spite of the reduced diameter. When the distal end is formed to have a wall thickness larger than that of the proximal end, the tubular body can be easily formed with an edge of special shape at its distal end, or formed with a groove extending along the outer surface of the distal portion of the needle in the longitudinal direction to thereby enable visual confirmation of the access to the vein. Formation of the distal end with a wall thickness larger than that of the proximal end also prevents a large amount of drug solution from being administered at once and enables slow release of the drug solution at a low rate. When the tubular body manufactured is the one comprising a plurality of sections each having different diameter as in the case of the tubular body with a stepped lateral shape, each section can be formed to have a different wall thickness so that the resulting tubular body is free from the problem of insufficient strength inherent to the tubular body of consistent wall thickness manufactured by drawing.

The method of the present invention has enabled to produce a tubular body of small diameter which has a wall thickness varying along its longitudinal axis as well as a smooth surface without causing defects such as grinding mark on the surface of the tubular body that had been inevitably produced in the conventional method wherein the tubular body had been manufactured by grinding the inner or the outer surface. This method can also be used in the mass production of the tubular body since no additional step of grinding the inner or outer surface is required in its production.

What is claimed is:

1. A method for manufacturing a metal tubular body in which at least a part of a wall thickness of the tubular body varies along its longitudinal axis and the tubular body has a minimum inner diameter of up to 2 mm and a maximum wall thickness of up to 0.5 mm, and an inner surface of the tubular body has a maximum height difference (Rf) of surface roughness as defined by JIS-B-0601-1944 of up to 3 $\mu$m, comprising:

punching a sheet blank in developed shape of the tubular body from a metal sheet such that the metal sheet and the sheet blank remain partly joined, said metal sheet having at least a part possessing a thickness which varies in the direction of the longitudinal axis of the finished tubular body;

pressing the sheet blank into a tubular shape; and cutting the pressed sheet blank from the metal sheet to thereby produce the tubular body.

2. A method for manufacturing a metal tubular body according to claim 1 further comprising the steps of, after pressing the sheet blank in tubular shape, the tubular-shaped sheet blank is welded along its seam.

3. A metal tubular body manufactured by the method of claim 2.

4. A metal tubular body manufactured by the method of claim 1.

5. A method for manufacturing a metal tubular body according to claim 1, further comprising cutting a distal end of the tubular body at an angle to the longitudinal axis of the tubular body to form a beveled surface at the distal end of the tubular body.

6. A method for manufacturing a metal tubular body in which at least a part of a wall thickness of the tubular body varies along its longitudinal axis and the tubular body has a minimum inner diameter of up to 2 mm and a maximum wall thickness of up to 0.5 mm, and an inner surface of the tubular body has a maximum height difference (Rf) of surface roughness as defined by JIS-B-0601-1994 of up to 3 $\mu$m, comprising:

punching a sheet blank in a developed shape of the tubular body from a metal sheet such that the metal sheet and the sheet blank remain partly joined;

pressing the sheet blank into a tubular shape such that the pressed sheet blank in tubular shape has at least a part possessing a thickness which varies along the longitudinal axis; and cutting apart the metal sheet and the sheet blank at the part where they remain joined to thereby produce the tubular body.

7. A metal tubular body manufactured by the method of claim 6.

8. A method for manufacturing a metal tubular body according to claim 6, further comprising cutting a distal end of the tubular body at an angle to the longitudinal axis of the tubular body to form a beveled surface at the distal end of the tubular body.

9. A method for manufacturing a metal tubular body in which at least a part of a wall thickness of the tubular body varies along its longitudinal axis, comprising:

punching from a metal sheet a sheet blank having a developed shape of the tubular body such that the metal sheet and the sheet blank remain partly joined, said metal sheet having, prior to any punching, at least a part possessing a thickness which varies in the direction of the longitudinal axis of the finished tubular body;

pressing the punched sheet blank into a tubular shape; and cutting the pressed sheet blank from the metal sheet to produce the tubular body.

10. A method for manufacturing a metal tubular body according to claim 9, further comprising cutting a distal end of the tubular body at an angle to the longitudinal axis of the tubular body to form a beveled surface at the distal end of the tubular body.

11. A method for manufacturing a metal tubular body according to claim 9, wherein the punched sheet blank is pressed into the tubular shape by bringing longitudinal edges of the punched sheet blank together at a seam, and further comprising welding the tubular body along the seam after pressing the sheet blank into the tubular shape.

12. A method for manufacturing a metal tubular body according to claim 9, wherein the tubular body has a minimum inner diameter of up to 2 mm and a maximum wail thickness of up to 0.5 mm, and an inner surface of the tubular body has a maximum height difference (Rf) of surface roughness as defined by JIS-B-0601-1994 of up to 3 $\mu$m.

* * * * *

UNITED STATES PATENT AND TRADEMARK OFFICE
CERTIFICATE OF CORRECTION

| | |
|---|---|
| PATENT NO. | : 6,748,786 B2 |
| APPLICATION NO. | : 10/375085 |
| DATED | : June 15, 2004 |
| INVENTOR(S) | : Tetsuya Ooyauchi et al. |

It is certified that error appears in the above-identified patent and that said Letters Patent is hereby corrected as shown below:

On title page
Item (73), after "Okano Kogyo Co., Ltd.," change "Hyogo" to --Tokyo--.

Signed and Sealed this

Twenty-eighth Day of August, 2007

JON W. DUDAS
*Director of the United States Patent and Trademark Office*